(12) United States Patent
Yin

(10) Patent No.: US 10,167,869 B2
(45) Date of Patent: Jan. 1, 2019

(54) WASTEWATER AND ANALYSIS SYSTEM WITH MONITORED SAMPLE TUBE FILL LEVEL

(71) Applicant: Wuhan China Star Optoelectronics Technology Co., Ltd., Wuhan, Hubei (CN)

(72) Inventor: Yanping Yin, Guangdong (CN)

(73) Assignee: Wuhan China Star Optoelectronics Technology Co., Ltd, Wuhan, Hubei (CN)

( * ) Notice: Subject to any disclaimer, the term of this patent is extended or adjusted under 35 U.S.C. 154(b) by 192 days.

(21) Appl. No.: 15/112,365

(22) PCT Filed: May 23, 2016

(86) PCT No.: PCT/CN2016/083013
§ 371 (c)(1),
(2) Date: Jul. 18, 2016

(87) PCT Pub. No.: WO2017/128570
PCT Pub. Date: Aug. 3, 2017

(65) Prior Publication Data
US 2018/0094630 A1 Apr. 5, 2018

(30) Foreign Application Priority Data

Jan. 25, 2016 (CN) .......................... 2016 1 0047624

(51) Int. Cl.
*G01N 1/14* (2006.01)
*F04D 9/02* (2006.01)
(Continued)

(52) U.S. Cl.
CPC ................. *F04D 9/02* (2013.01); *G01N 1/14* (2013.01); *G01N 1/2035* (2013.01); *G01N 33/18* (2013.01);
(Continued)

(58) Field of Classification Search
CPC .......... F04D 9/02; G01N 1/14; G01N 1/2035; G01N 33/18; G01N 1/18; G01N 35/1095
(Continued)

(56) References Cited

U.S. PATENT DOCUMENTS 4,067,663 A * 1/1978 Brooks ................... F04D 9/042
417/199.2
5,091,863 A * 2/1992 Hungerford .............. E03F 7/00
141/1
(Continued)

FOREIGN PATENT DOCUMENTS

CN 2659982 Y 12/2004
CN 1862024 A 11/2006
(Continued)

*Primary Examiner* — Natalie F Huls
*Assistant Examiner* — Monica S Young
(74) *Attorney, Agent, or Firm* — Andrew C. Cheng

(57) ABSTRACT

The present invention discloses an online monitoring system, comprising a self-priming pump, a first sample pipe and a container containing a sample to be tested, and the first sample pipe connects the self-priming pump and the container, and the self-priming pump transports the ample to be tested in the container to the first sample pipe; the online monitoring system further comprises a fluid supplementation device connected with the first sample pipe, and a default level value is preset in the fluid supplementation device, and the fluid supplementation device monitors a level of the sample to be tested in the first sample pipe, and extracts the sample to be tested from the container to supplement to the first sample pipe as the level value of the sample to be tested in the first sample pipe is lower than the default level value.

10 Claims, 2 Drawing Sheets

(51) Int. Cl.
   *G01N 33/18* (2006.01)
   *G01N 1/20* (2006.01)
   *G01N 1/18* (2006.01)
   *G01N 35/10* (2006.01)

(52) U.S. Cl.
   CPC ........... *G01N 1/18* (2013.01); *G01N 35/1095* (2013.01); *G01N 2001/1418* (2013.01)

(58) Field of Classification Search
   USPC ....................................................... 73/64.56
   See application file for complete search history.

(56) References Cited

U.S. PATENT DOCUMENTS

| | | | | |
|---|---|---|---|---|
| 5,695,719 | A | * | 12/1997 | Lynggaard ............. B01D 61/28 422/504 |
| 5,864,140 | A | * | 1/1999 | Owens ................... G01N 21/05 250/343 |
| 2012/0037234 | A1 | * | 2/2012 | Eckman ............... B01D 29/035 137/1 |
| 2016/0185616 | A1 | * | 6/2016 | Wright .................... C02F 1/008 210/137 |
| 2016/0187311 | A1 | * | 6/2016 | Brooking ........... G01N 33/1886 435/29 |

FOREIGN PATENT DOCUMENTS

| | | | |
|---|---|---|---|
| CN | 101625001 A | 1/2010 | |
| CN | 201780291 U | 3/2011 | |
| CN | 203733016 U | 7/2014 | |
| CN | 204265811 U | 4/2015 | |
| CN | 104595199 A | 5/2015 | |
| CN | 204419604 U | 6/2015 | |
| CN | 204783703 U | 11/2015 | |
| CN | 204945153 U | 1/2016 | |
| DE | 102012112541 A1 * | 6/2014 | ............. G01N 21/05 |
| JP | 58-110894 A | 7/1983 | |
| JP | 4128062 B2 | 7/2008 | |
| WO | 2008/047159 A1 | 4/2008 | |

* cited by examiner

WASTEWATER AND ANALYSIS SYSTEM WITH MONITORED SAMPLE TUBE FILL LEVEL

CROSS REFERENCE

This application claims the priority of Chinese Patent Application No. 201610047624.8, entitled "Online monitoring system", filed on Jan. 25, 2016, the disclosure of which is incorporated herein by reference in its entirety.

FIELD OF THE INVENTION

The present invention relates to an online monitoring technical field, and more particularly to an online monitoring system.

BACKGROUND OF THE INVENTION

At present, the most of the manufacture factories is equipped with the online monitoring system of the waste water pollution source. The self-priming pump is used in the online monitoring system to perform water quality sampling to the pollution source according to prior art. For that the self-priming pump must normally work, it needs enough water in the sample pipe connected with the self-priming pump. In the drain process of the large amount of the industry waste water, the bacteria growth phenomenon occurs to the waste water flowing through the sample pipe check valve, and may easily cause that the check valve is blocked and cannot be deactivated, and then the sample pipe loses the water. Thus, the self-priming pump cannot normally work. Then, it results in that the monitoring data of the online monitor is not normal.

SUMMARY OF THE INVENTION

An objective of the present invention is to provide an online monitoring system, for ensuring that the monitor can constantly performed.

An online monitoring system, comprising a self-priming pump, a first sample pipe and a container containing a sample to be tested, and the first sample pipe connects the self-priming pump and the container, and the self-priming pump transports the ample to be tested in the container to the first sample pipe; the online monitoring system further comprises a fluid supplementation device connected with the first sample pipe, and a default level value is preset in the fluid supplementation device, and the fluid supplementation device monitors a level of the sample to be tested in the first sample pipe, and extracts the sample to be tested from the container to supplement to the first sample pipe as the level value of the sample to be tested in the first sample pipe is lower than the default level value.

The fluid supplementation device comprises a level sensing switch, a pump unit and a fluid supplementation pipe, and the level sensing switch is electrically connected to both the first sample pipe and the pump unit, and the pump unit extracts the sample to be tested from the container and transports the same to the fluid supplementation pipe, and the fluid supplementation pipe is connected with the pump unit and the first sample pipe.

The level sensing switch comprises one of a capacitance type level switch, a floating ball type level switch, an electronic level switch, an ultrasonic and a pitchfork level switch.

The pump unit is an immersible pump.

The fluid supplementation device further comprises a filter unit, and the filter unit is located between the pump unit and the container, and one end of the filter unit is connected to the pump unit and the other end is connected to the container.

The container is a pap tank.

The online monitoring system further comprises an online monitor and a second sample pipe, and the second sample pipe is connected to the online monitor and the self-priming pump, and the online monitor is electrically connected to the self-priming pump and the fluid supplementation device, respectively.

The online monitoring system further comprises a drain pipe, and the drain pipe is connected to the online monitor and the container.

Based on the aforesaid technical solution, the online monitoring system provided by the present invention is installed with the fluid supplementation device, and the fluid supplementation device can supplement the sample to be tested in the first sample pipe to ensure that the self-priming pump normally work when the level value of the sample to be tested in the first sample pipe is lower than the default level value. Thus, it can ensure that the online monitoring system can normally and constantly perform monitoring.

BRIEF DESCRIPTION OF THE DRAWINGS

In order to more clearly illustrate the embodiments of the present invention, the following figures will be described in the embodiments are briefly introduced. It is obvious that the drawings are only some embodiments of the present invention, those of ordinary skill in this field can obtain other figures according to these figures without paying the premise.

DETAILED DESCRIPTION OF PREFERRED EMBODIMENTS

Embodiments of the present invention are described in detail with the technical matters, structural features, achieved objects, and effects with reference to the accompanying drawings as follows. It is clear that the described embodiments are part of embodiments of the present invention, but not all embodiments. Based on the embodiments of the present invention, all other embodiments to those of ordinary skill in the premise of no creative efforts obtained, should be considered within the scope of protection of the present invention.

Figure 1:
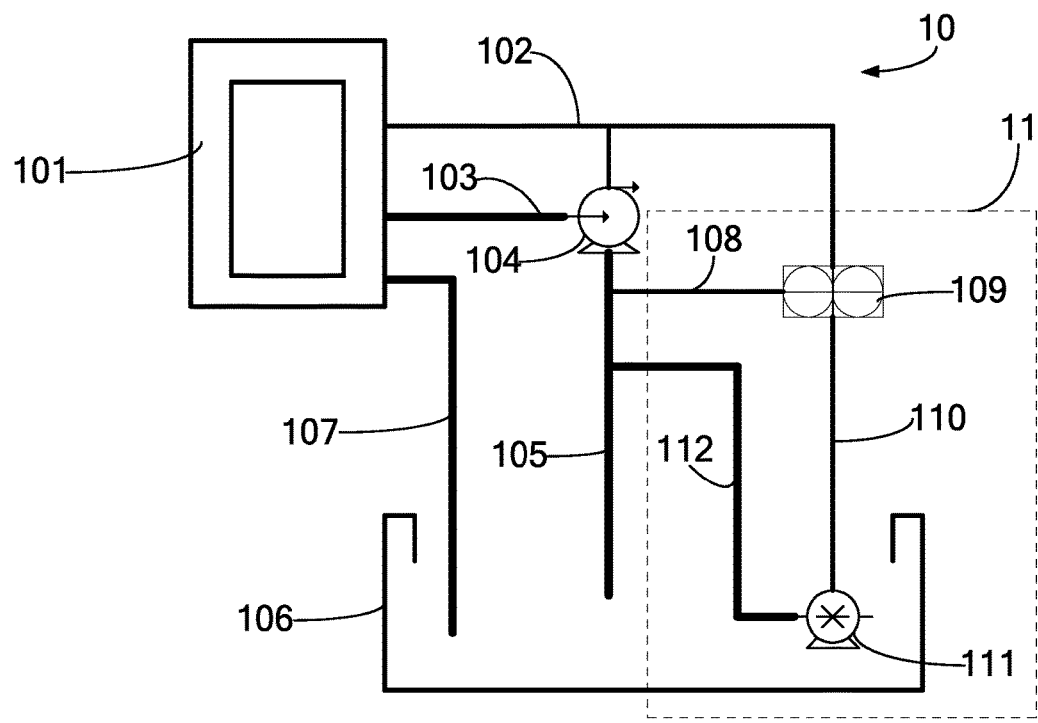
FIG. 1 is a structure diagram of an online monitoring system provided by the embodiment of the present invention.

As shown in FIG. 1, an online monitoring system 10 according to the embodiment of the present invention comprises an online monitor 101, a power source line 102, a second sample pipe 103, a self-priming pump 104, a first sample pipe 105, a pap tank 106, a drain pipe 107 and a fluid supplementation device 11.

The online monitor 101 is electrically connected to the self-priming pump 104 through the power source line 102, and the online monitor 101 controls on and off of the self-priming pump 104. Meanwhile, the online monitor 101 can perform test to the sample to be tested which is sampled to monitor the pollution condition. The second sample pipe 103 is connected to an outlet of the self-priming pump 104 and the online monitor 101. The first sample pipe 105 is connected to an inlet of the self-priming pump 104 and the pap tank 106. The drain pipe 107 is connected to the online monitor 101 and the pap tank 106. Therefore, the self-priming pump 104 is activated to work under the control of the online monitor 101 and extracts the sample to be tested from the pap tank 106 through the first sample pipe 105, and transports the sample to be tested to the online monitor 101 through the second sample pipe 103. After the online monitor 101 performs the test to the sample to be tested, the sample waste fluid is drained to the pap tank 106 through the drain pipe 107. In this embodiment, the pap tank is employed to contain the sample to be tested; in other embodiment, other containers can be used for containing the sample to be tested.

When the level of the sample to be tested in the first sample pipe 105 is too low, and the self-priming pump 104 cannot work. Then, it results in that the monitoring data of the online monitor 101 is not normal. The fluid supplementation device 11 can supplement the sample to be tested in the first sample pipe 105 to ensure that the self-priming pump 104 can normally work.

In this embodiment, the fluid supplementation device 11 comprises a signal line 108, a level sensing switch 109, a power source line 110, an immersible pump 111 and a fluid supplementation pipe 112. In other embodiment, the fluid supplementation device can comprise other components as long as that the fluid supplementation device can act function of supplementing the sample to be tested to ensure that the immersible pump can normally work.

In this embodiment, the level sensing switch 109 is connected to the online monitor 101 through the power source line 102, and the online monitor 101 controls the power supply of the level sensing switch 109. The power source line 110 is provided between the level sensing switch 109 and the immersible pump 111. The level sensing switch 109 controls on and off of the immersible pump 111 through the power source line 110. The signal line 108 is provided between the level sensing switch 109 and the first sample pipe 105. Through the signal line 108, the level sensing switch 109 can monitor the level of the sample to be tested in the first sample pipe 105. A default level value is preset in the level sensing switch 109. The default level value is a level value, which the sample to be tested in the first sample pipe 105 should reach, capable of ensuring that the self-priming pump 104 can normally work. The default level value is determined according to the practical condition. In this embodiment, the level sensing switch 109 comprises a capacitance type level switch, a floating ball type level switch, an electronic level switch, an ultrasonic or a pitchfork level switch but is not limited thereto.

The immersible pump 111 is in the pap tank 106, and is employed to extract the sample to be tested in the pap tank 106. The volume of the immersible pump is small, and the structure is compacted, and the reliability is high. In other embodiments, other pump units can replace the immersible pump. The fluid supplementation pipe 112 is provided between the immersible pump 111 and the first sample pipe 105. The immersible pump 111 pumps the extracted sample to be tested into the fluid supplementation pipe 112. The sample to be tested flows into the first sample pipe 105 through the fluid supplementation pipe 112.

When the online monitoring system 10 of this embodiment works, the level sensing switch 109 monitors the level of the sample to be tested in the first sample pipe 105. When the level value of the sample to be tested in the first sample pipe 105 is lower than the default level value, the self-priming pump 104 cannot normally work. Then, the level sensing switch 109 activates the immersible pump 111, and the immersible pump 111 extracts the sample to be tested from the pap tank 106, and pumps the sample to be tested into the fluid supplementation pipe 112. The sample to be tested in the fluid supplementation pipe 112 flows into the first sample pipe 105 to make the level of the sample to be tested in the first sample pipe 105 rise up. When the level value of the sample to be tested in the first sample pipe 105 reaches the default level value, the level sensing switch 109 deactivates the immersible pump 111. The immersible pump 111 stops extracting the sample to be tested. The sample to be tested in the first sample pipe 105 stops increasing. Accordingly, the level of the sample to be tested is kept at the default level value, and thus it can be ensured that the self-priming pump 104 can normally work.

Thus, the online monitoring system 10 of this embodiment is installed with the fluid supplementation device 11, and the fluid supplementation device 11 can supplement the sample to be tested in the first sample pipe 105 to ensure that the self-priming pump 104 normally work when the level value of the sample to be tested in the first sample pipe 105 is lower than the default level value. Thus, it can ensure that the online monitoring system 10 can normally and constantly perform monitoring.

Figure 2:
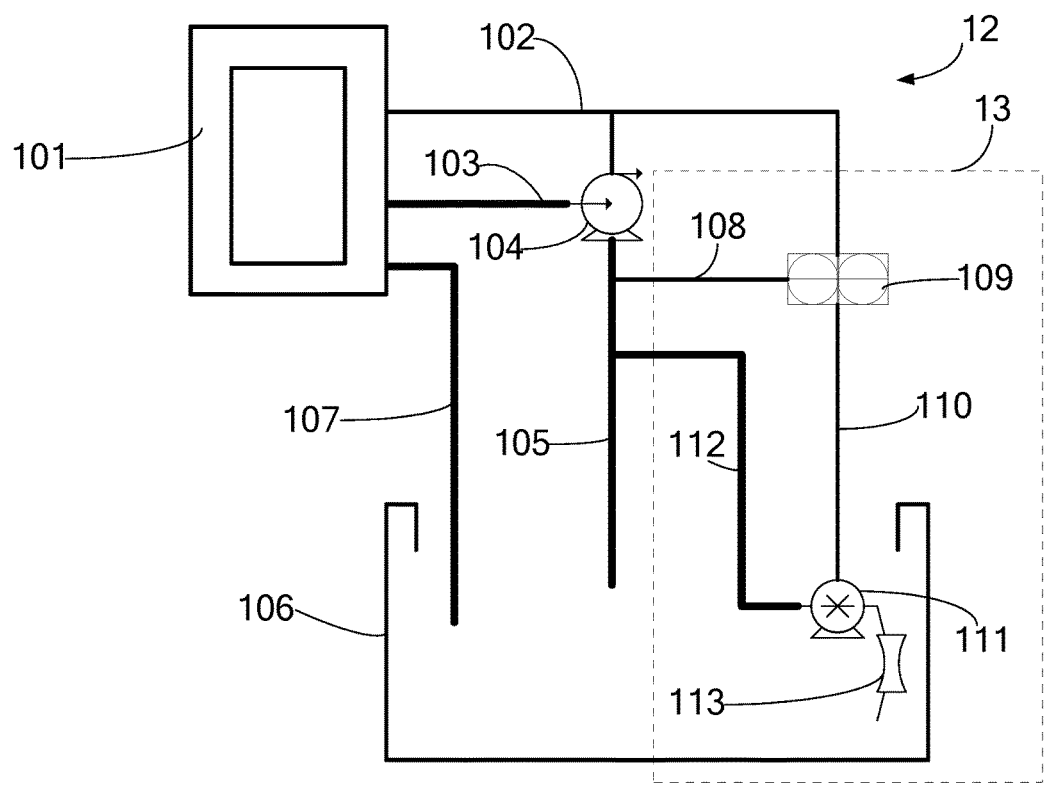
FIG. 2 is a structure diagram of an online monitoring system provided by another embodiment of the present invention.

As shown in FIG. 2, in another embodiment of the present invention, the difference from the aforesaid embodiment is: in the online monitoring system 12, the fluid supplementation device 13 further comprises a filter unit 113. The filter unit 113 can clean and filter the impurity substance in the sample to be tested. The filter unit 113 is provided between the immersible pump 111 and the pap tank 106. One end of the filter unit 113 is connected to the immersible pump 111 and the other end is connected to the pap tank 106. The sample to be tested in the pap tank 106 passes through the filter unit 113, and then is extracted by the immersible pump 111, to prevent the impurity substance in the sample to be tested blocking the immersible pump 111.

The foregoing descriptions are merely the specific embodiments of the present invention. However, the present invention is not limited thereby. Any modifications, equivalent replacements or improvements within the spirit and principles of the embodiment described above, which can be easily derived by those skilled persons in this art from the technical field disclosed in the present invention should be covered by the protected scope of the invention. Thus, the patent protection scope of the present invention should be subjected to what is claimed is.

What is claimed is:

1. A wastewater monitor and analysis system, comprising a self-priming pump, a first sample pipe and a container, which is a Parshall flume tank, containing a sample to be tested, and the first sample pipe connects the self-priming pump and the container, and the self-priming pump transports the sample to be tested in the container to the first sample pipe, wherein the wastewater monitor and analysis system further comprises a fluid supplementation device connected with the first sample pipe, and a default level value is preset in the fluid supplementation device, and the fluid supplementation device monitors a level of the sample to be tested in the first sample pipe, and extracts the sample to be tested from the container to supplement the sample to be tested to the first sample pipe as the level value of the sample to be tested in the first sample pipe is lower than the default level value to ensure that the self-priming pump normally work and to ensure that the wastewater monitor and analysis system normally and constantly perform monitoring.

2. The wastewater monitor and analysis system according to claim 1, wherein the fluid supplementation device comprises a level sensing switch, a pump unit and a fluid supplementation pipe, and the level sensing switch is electrically connected to both the first sample pipe and the pump unit, and the pump unit extracts the sample to be tested from the container and transports the same to the fluid supplementation pipe, and the fluid supplementation pipe is connected with the pump unit and the first sample pipe.

3. The wastewater monitor and analysis system according to claim 2, wherein the level sensing switch comprises one of a capacitance type level switch, a floating ball type level switch, an electronic level switch, an ultrasonic and a pitchfork level switch.

4. The wastewater monitor and analysis system according to claim 3, wherein the pump unit is an immersible pump.

5. The wastewater monitor and analysis system according to claim 3, wherein the fluid supplementation device further comprises a filter unit, and the filter unit is located between the pump unit and the container, and one end of the filter unit is connected to the pump unit and the other end is connected to the container.

6. The wastewater monitor and analysis system according to claim 5, wherein the online monitoring system further comprises a drain pipe, and the drain pipe is connected to the online monitor and the container.

7. The wastewater monitor and analysis system according to claim 2, wherein the pump unit is an immersible pump.

8. The wastewater monitor and analysis system according to claim 2, wherein the fluid supplementation device further comprises a filter unit, and the filter unit is located between the pump unit and the container, and one end of the filter unit is connected to the pump unit and the other end is connected to the container.

9. The wastewater monitor and analysis system according to claim 8, wherein the wastewater monitor and analysis system further comprises a monitor equipment and a second sample pipe, and the second sample pipe is connected to the monitor equipment and the self-priming pump, and the monitor equipment is electrically connected to the self-priming pump and the fluid supplementation device, respectively to control on and off of the self-priming pump and the fluid supplementation device, respectively.

10. The wastewater monitor and analysis system according to claim 1, wherein the wastewater monitor and analysis system further comprises a monitor equipment and a second sample pipe, and the second sample pipe is connected to the monitor equipment and the self-priming pump, and the monitor equipment is electrically connected to the self-priming pump and the fluid supplementation device, respectively to control on and off of the self-priming pump and the fluid supplementation device, respectively.

\* \* \* \* \*